United States Patent [19]

Martens et al.

[11] Patent Number: 4,762,958

[45] Date of Patent: Aug. 9, 1988

[54] PROCESS AND FURNACE FOR THE STEAM CRACKING OF HYDROCARBONS FOR THE PREPARATION OF OLEFINS AND DIOLEFINS

[75] Inventors: André Martens; Serge Bellet, both of Chateauneuf les Martigues, France

[73] Assignee: Naphtachimie S.A., Tour Neptune, France

[21] Appl. No.: 62,885

[22] Filed: Jun. 16, 1987

[30] Foreign Application Priority Data

Jun. 25, 1986 [FR] France .................................. 86 09219
Jun. 25, 1986 [FR] France .................................. 86 09221

[51] Int. Cl.$^4$ ........................... C07C 4/04; C10G 9/00
[52] U.S. Cl. ..................................... 585/613; 208/106; 208/132; 585/615; 585/614; 585/648; 585/649; 585/650
[58] Field of Search ............... 585/613, 615, 648, 649, 585/650; 208/106, 132

[56] References Cited

U.S. PATENT DOCUMENTS

| | | | |
|---|---|---|---|
| 2,994,724 | 8/1961 | Hillard et al. | 208/132 |
| 3,112,880 | 12/1963 | Pollock | 208/132 |
| 3,306,844 | 2/1967 | Briefley et al. | 208/132 |
| 4,342,642 | 8/1982 | Bauer et al. | 208/132 |

FOREIGN PATENT DOCUMENTS

| | | | |
|---|---|---|---|
| 1165907 | 10/1969 | United Kingdom | 208/132 |
| 1177181 | 1/1970 | United Kingdom | 208/132 |

*Primary Examiner*—Asok Pal
*Attorney, Agent, or Firm*—Brooks Haidt Haffner & Delahunty

[57] ABSTRACT

The present invention relates to a process for the preparation of olefins by the cracking of hydrocarbons consisting in passing a mixture of hydrocarbons and steam flowing in a cracking tube disposed inside a radiation zone of a furnace. The process is characterized in that an increase of the cracking temperature of the mixture between the inlet and the outlet of the radiation zone is associated to a non-homogeneous distribution of the thermal power of the furnace, greater at the beginning of the cracking tube than at the end, and to a reaction volume which is greater in the second half of the length tube than in the first one.

The present invention relates also to a cracking furnace in which between the inlet and the outlet of the radiation zone the diameter of the cracking tube increases and the thermal power of the heating means decreases.

8 Claims, 4 Drawing Sheets

PROCESS AND FURNACE FOR THE STEAM CRACKING OF HYDROCARBONS FOR THE PREPARATION OF OLEFINS AND DIOLEFINS

The invention relates to a process for the cracking of hydrocarbons in the presence of steam with the purpose of preparing olefins and diolefins, more particularly ethylene. The invention also relates to an apparatus formed by a cracking furnace intended for the performance of the process.

It is known to crack with steam liquid hydrocarbons having 5 to 15 carbon atoms, such as naphtha, light gasolines and gas oil, in furnaces whose outlet temperature is generally between 750° C. and 850° C., or gaseous hydrocarbons, such as alkanes having 2 to 4 carbon atoms, possibly mixed with methane and/or alkenes having 2 to 4 carbon atoms, in furnaces whose outlet temperature is generally between 800° C. and 880° C. In this process, known as steam cracking or pyrolysis, a mixture of hydrocarbons and steam flowing in a cracking tube disposed in the form of a coil inside a furnace is passed through the radiant portion thereof, the pressure of the mixture at the outlet of the furnace being generally between 120 kPa and 240 kPa. The hydrocarbons are therefore more particularly converted on the one hand into a gaseous hydrocarbonated fraction comprising more particularly olefins having 2 to 6 carbon atoms, such as ethylene, propylene and isobutene, and diolefins, such as butadiene and also into a liquid hydrocarbonated fraction known as "steam cracking gasoline" comprising hydrocarbons having 5 to 12 carbon atoms, and into undesirable byproducts, such as methane.

As a rule, in steam cracking processes more particularly using liquid hydrocarbons the cracking yield of ethylene is determined by the ratio by weight between the quantity of ethylene produced and the quantity of hydrocarbons used. The level of conversion by weight of the hydrocarbons used is also determined by the following equation:

Level of conversion by weight equals 100 −

(% by weight of the hydrocarbonated fraction at the furnace outlet, having an ASTM distillation range of 45/205° C.).

The prior art steam cracking processes are performed with the object of obtaining the highest possible cracking yield of ethylene. Steam cracking furnaces are therefore generally designed to operate in heavy duty conditions. The conditions are more particularly such that the mixture of hydrocarbons and steam flows for a relatively short time, generally less than one second, through a cracking tube. The cracking temperature selected is also generally the highest possible value, but it is limited by the thermal stresses of the furnace and the cracking tube. The thermal stresses of the cracking tube, which are mainly connected with its skin temperature, depend on the nature of the metal or alloy from which the cracking tube is made. The pressure of the mixture flowing in the cracking tube is also as a rule relatively low, so as to limit the development of secondary reactions. The steam cracking furnace also comprises a heating device formed by burners disposed on the grid and/or the internal walls of the furnace. The thermal power of the heating device is generally distributed homogeneously along the cracking tube, so that the mixture of liquid hydrocarbons and steam is subjected to a temperature which increases rapidly in the first part of the tube, then more slowly in the second part of the tube. In these conditions the ethylene yield of a steam cracking furnace of given size is of course mainly limited by the thermal stresses of the cracking tube and considerable disadvantages may occur, such as coking inside the cracking tube and its premature ageing.

It was already suggested a long time ago by British Patent No. 1 177 181 that to reduce the coking the thermal power should be applied non-uniformly along a cracking tube of constant section, more particularly more intensely at the start of the tube than at its termination. A very slightly increased yield of ethylene was observed, but it remained limited to about 1%. It was also found that the level of hydrocarbon conversion by weight is not enhanced by such a process.

It has also been known for a long time, for example, from French Patent No. 2 227 314 that with a view to increasing the flow rate of the hydrocarbons to be cracked, the cracking tubes can be combined in pairs so as to form one tube having a proportionately larger cross-section. Thus the section of the various tubes increases in the direction of flow of the hydrocarbons to be cracked, and this enables a greater quantity of heat to be transmitted to the hydrocarbons for the same temperature, thereby improving the distribution of the skin temperature of the cracking tubes. However, such an apparatus does not substantially enhance the ethylene yield or the rate of hydrocarbon conversion by weight.

It is also known that, having regard to the considerable size of industrial steam cracking plants, it is always essential to enhance not only the yield and hourly production of ethylene by a steam cracking furnace of given size, but also to enhance the level of hydrocarbon conversion by weight.

However, having regard to the considerable cost of investment in this type of industrial installation, it is economically impermissible that the modifications envisaged to achieve this aim should result in excessive and expensive conversions of the existing steam cracking installations. Important studies have therefore been carried on for several years in this field and unceasing research efforts made at both the laboratory and industrial stage.

A process has now been found and also an apparatus formed by a furnace for cracking hydrocarbons in the presence of steam, which allow a very substantial enhancement not only of the ethylene yield of cracking, but also of the level of hydrocarbon conversion by weight. The process and apparatus according to the invention can moreover be readily adapted to the existing installations for the steam cracking of hydrocarbons.

The invention relates firstly to a process for the preparation of olefins and diolefins by the cracking of hydrocarbons in the presence of steam, wherein a mixture of hydrocarbons and steam flowing in a cracking tube disposed inside a furnace radiation zone is passed through such zone in a dwell time of between 300 and 1800 milliseconds at a furnace outlet pressure of between 120 and 240 kPa, the process being characterized in that (a) the cracking temperature of the mixture of hydrocarbons and steam increases from the inlet temperature of the radiation zone of between 500° and 700° C. to the outlet temperature of such zone of between 800° and 880° C., the increase in temperature being associated with a non-homogeneous distribution of the thermal power of the furnace applied along the cracking tube, the distribution being such that the thermal power applied to the first half of the tube length, situated towards the inlet of the radiation zone, is 1.5 to 5 times greater than that applied to the second half of the tube length, situated towards the outline of such zone, and (b) the reaction volume of the second half of the length of the cracking tube, situated towards the outlet of the radiation zone, is 1.3 to 4 times greater than that of the first half of the tube length, situated towards the inlet of such zone.

The process according to the invention is firstly characterized by the development of the cracking temperature of the mixture of hydrocarbons and steam flowing in the tube. The temperature increases along the cracking tube, between the inlet and the outlet of the radiation zone of the furnace—i.e., in the direction in which the mixture flows. More particularly, the cracking temperature of the mixture of hydrocarbons and steam is between 500° C. and 700° C. at the inlet of the furnace radiation zone, preferably between 550° C. and 660° C.; at the outlet of the zone it is between 800° C. and 880° C., preferably between 820° C. and 860° C. Preferably the mixture of hydrocarbons and steam is generally subjected to preheating before it enters the radiation zone of the furnace; such preheating can be performed by any known means, more particularly in a heating zone by the convection of the furnace.

The process according to the invention is also characterized in that the increase in the cracking temperature of the mixture is considerably greater in the first half of the tube length, situated towards the inlet of the furnace radiation zone, than in the second half of the tube length, situated towards the outlet of the zone. The cracking temperature of the mixture of hydrocarbons and steam flowing in the tube between the inlet and outlet of the furnace radiation zone is controlled by a non-homogeneous distribution of the thermal power applied to the tube. More particularly, the thermal power applied to the first half of the tube length, situated towards the inlet of the furnace radiation zone, is 1.5 to 5 times greater, preferably 2 to 4 times greater than that applied to the second half of the tube length, situated towards the outlet of such zone, more particularly when gaseous hydrocarbons are used in the process. It can be 1.5 to 4 times greater, preferably 2 to 3 times greater than that applied to the second half of the tube length, when the process more particularly uses liquid hydrocarbons. The term thermal power is taken to mean the quantity of heat contributed per unit of time and unit of volume of the furnace enclosing the cracking tube.

The mean dwell time of the mixture of hydrocarbons and steam flowing in the cracking tube between the inlet and the outlet of the furnace radiation zone is generally between 300 and 1800 milliseconds, preferably between 400 and 1400 milliseconds, more particularly when gaseous hydrocarbons are used. It is generally between 300 and 1000 milliseconds, preferably between 400 and 800 milliseconds, in the case of liquid hydrocarbons.

The process according to the invention is also characterized by the reaction volume of the cracking tube, which is not identical in the first and second halves of the tube length. More precisely, the reaction volume of the second half of the cracking tube length, situated towards the outlet of the radiation zone, is 1.3 to 4 times greater, preferably 1.5 to 2.5 time greater than that of the first half of the tube length, situated towards the inlet of such zone. Moreover, the reaction volume per unit of cracking tube length increases continuously or discontinuously from the inlet to the outlet of the furnace radiation zone. In practice it is preferred to perform the increase discontinuously—i.e., in stages along the cracking tube.

It is found that in these conditions the combination of a non- homogeneous distribution of the thermal power of the radiation furnace, applied along the cracking tube, with a reaction volume increasing per unit of cracking tube length results in an appreciable enhancement of the mean dwell time of the mixture flowing in the second half of the cracking tube length.

The effect of this combination enables the mixture of hydrocarbons and steam to pass relatively quickly through that portion of the cracking tube where the cracking temperatures are lowest, but more slowly through that portion of the tube where the cracking temperatures are highest. Unexpectedly, the result of the process according to the invention is not only to enhance the hourly yield and production of ethylene, but also the level of hydrocarbon conversion by weight in a furnace of given size, with a cracking tube of given skin temperature. This result is moreover obtained with a substantial increase in the maximum cracking capacity of a furnace of given size.

The composition of the mixture of hydrocarbons and steam used in the process according to the invention is such that the ratio by weight between the quantity of hydrocarbons and the quantity of steam is between 1 and 10, preferably between 2 and 6.

The hydrocarbons used in the mixture with steam can be liquid hydrocarbons selected from naphtha, formed by hydrocarbons having about 5 to 10 carbon atoms, the light gasolines formed by hydrocarbons having about 5 or 6 carbon atoms, gas oil, formed by hydrocarbons having about 8 to 15 carbon atoms, and their mixtures. They can also be used mixed with saturated and unsaturated hydrocarbons having 3 to 6 carbon atoms. They can also be gaseous hydrocarbons formed by alkanes having 2 to 4 carbon atoms or by their mixtures. The alkanes can be used possibly mixed with alkenes having 2 to 6 carbon atoms and/or methane and/or alkanes having 5 or 6 carbon atoms. More particularly in the process according to the invention use can be made of natural gas, liquefied petroleum gas (LPG), or ethane, a byproduct of the steam cracking of liquid hydrocarbons such as naphtha or gas oil.

The invention also relates to an apparatus formed by a furnace for cracking hydrocarbons in the presence of steam, comprising a thermal radiation enclosure which has heating means and through which at least one cracking tube extends in which the mixture of steam and hydrocarbons for cracking flows, the apparatus being characterized in that (a) the internal diameter of the cracking tube increases continuously or discontinuously from the inlet to the outlet of the thermal radiation enclosure, so that the ratio between the internal diameters of the tube at the outlet and the inlet of such enclosure is between 1.3 and 3, and (b) the heating means are formed by burners whose thermal power diminishes along the cracking tube from the inlet to the outlet of the thermal radiation enclosure, so that the ratio between the thermal power of the burners applied to the first half of the length of the cracking tube, situated towards the inlet of the thermal radiation enclosure, and that applied to the second half of the tube length, situated towards the outlet of such enclosure, is between 60/40 and 85/15.

The steam cracking furnace comprises a thermal radiation enclosure through which at least one cracking tube extends in the form of a horizontal or vertical coil. However, the mean internal diameter of the tube length must remain within ranges of values compatible with the mechanical and thermal stresses to which the materials of which the cracking tube is made are subjected. More particularly the mean internal diameter of the cracking tube is between 70 mm and 160 mm, preferably between 80 mm and 150 mm.

The steam cracking furnace according to the invention comprises a cracking tube whose internal diameter increases continuously or discontinuously between the inlet and the outlet of the thermal radiation enclosure—i.e., in the direction in which the mixture of hydrocarbons and steam flows. More particularly the increase in the internal diameter of the cracking tube is such that the ratio between the internal diameters of the tube at the inlet and outlet of the thermal radiation enclosure is between 1.3 and 3, preferably between 1.6 and 2.2. In practice the internal diameter of the cracking tube at the inlet of the thermal radiation enclosure is preferably between 60 and 90 mm, that at the outlet of the enclosure being preferably between 110 and 200 mm. These values take account of the fact that the intention is to avoid an excessive increase in the load losses of the cracking tube, more particularly in the portion where the internal diameter of the tube is smallest. The increase in internal diameter can be continuous all along the cracking tube. However, it is preferred to use a cracking tube formed by a succession of tubes whose internal diameter increases from the inlet to the outlet of the thermal radiation enclosure of the furnace. The increase in the internal diameter of the cracking tube is more particularly such that the reaction volume of the second half of the tube length, situated towards the outlet of the radiation zone, is 1.3 to 4 time greater, preferably 1.5 to 2.5 times greater than that of the first half of the tube length, situated towards the inlet of such zone.

In practice the cracking tube is disposed in the form of a coil formed by a succession of straight portions interconnected by bends, the straight portions having internal diameters which increase from the inlet to the outlet of the thermal radiation enclosure.

In one variant, a cracking tube is used which after entering the thermal radiation enclosure of the furnace is divided into a cluster of parallel tubes whose internal diameter can be constant and whose number increases from the inlet to the outlet of the thermal enclosure, so that the reaction volume formed by the assembly of tubes corresponding to the second half of the cracking tube length is 1.3 to 4 times greater than that corresponding to the first half of the tube length.

Figure 1:
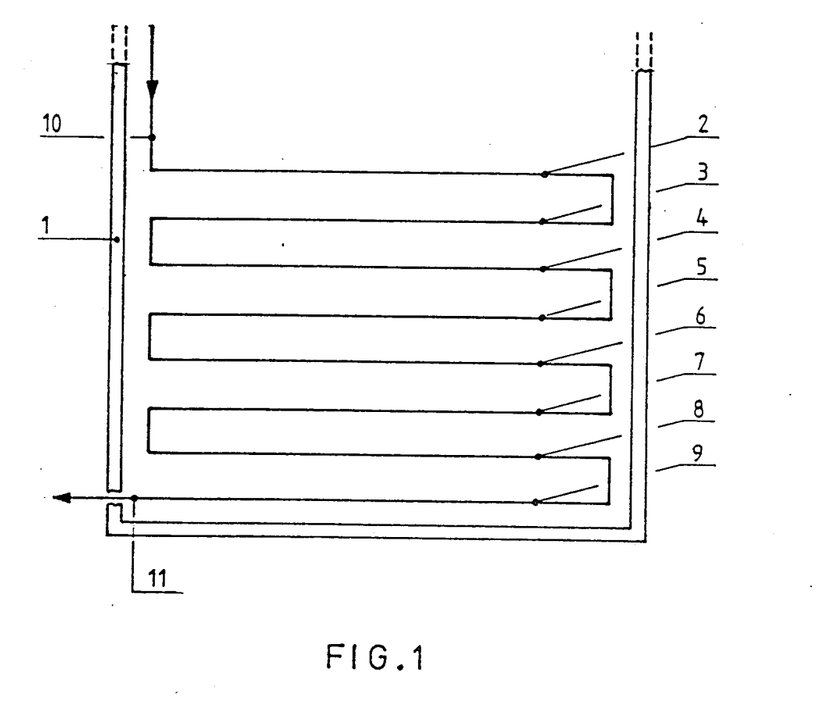
FIG. 1 illustrates diagrammatically a horizontal steam cracking furnace comprising a thermal radiation enclosure (radiation zone) through which a cracking tube extends in the form of a coil.

FIG. 1 illustrates diagrammatically a horizontal steam cracking furnace having a thermal radiation enclosure (1) through which a cracking tube extends which is disposed in the form of a coil formed by eight straight horizontal portions interconnected via bends, the sections (2) and (3) having an internal diameter of 81 mm, the sections (4) and (5) an internal diameter of 99 mm, the sections (6) and (7) an internal diameter of 117 mm, and the sections (8) and (9) an internal diameter of 135 mm, the inlet and outlet of the cracking tube in the thermal radiation enclosure having the references (10) and (11) respectively.

The steam cracking furnace according to the invention comprises a thermal radiation enclosure having heating means formed by burners disposed, for example, in rows on the grid and/or the walls of the enclosure. The arrangement, control and/or size of the burners in the thermal enclosure are such that the thermal power decreases along the cracking tube from the inlet to the outlet of the enclosure. More particularly the ratio between the thermal power of the burner supplied to the first half of the length of the cracking tube, situated towards the inlet of the enclosure, and that applied to the second half of the tube length, situated towards the outlet of the enclosure, is between 60/40 and 85/15, preferably between 67/33 and 80/20, and more particularly between 67/33 and 75/25. This decreasing profile of the thermal power of the burners applied along the cracking tube can readily be obtained by suitably controlling the flow rate of the gas or fuel gas supplied to each of the burners. Another way is dispose burners of appropriate size and calorific power in the thermal enclosure. At any rate, the maximum heating power must be such that the skin temperature does not exceed the limit compatible with the nature of the metal or alloy from which the cracking tube is made.

The following non-limitative Examples illustrate the invention.

EXAMPLE 1

A steam cracking furnace, such as that shown diagrammatically in FIG. 1, comprised a brickwork thermal radiation (1) formed by a rectangular parallelipiped whose internal dimensions were length: 9.75 m; width: 1.70 m and height: 4.85 m. Disposed in the enclosure (1) was a nickel and chromium based refractory steel cracking tube having a mean internal diameter of 108 mm, a thickness of 8 mm and, having regard to the capacity of the enclosure (1), a total length of 80 m between the inlet (10) and the outlet (11). The cracking tube was disposed in the form of a coil comprising 8 horizontal straight portions each of equal length which were interconnected via bends. The internal diameter of the sections (2) and (3) situated towards the inlet of the thermal enclosure was 81 mm; the following sections (4) and (5) had an internal diameter of 88 mm; then the sections (6) and (7) had an internal diameter of 117 mm;

the internal diameter of the sections (8) and (9) situated towards the outlet of the thermal enclosure was 135 mm.

Moreover, the internal diameters of the cracking tube at the inlet (10) and outlet (11) of the enclosure (1) being 81 mm and 135 mm respectively, the ratio between the internal diameters of the tube at the inlet and outlet was therefore 1.7. The reaction volume of the second half of the cracking tube length, corresponding to the straight sections (6), (7), (8), (9), was moreover 1.95 times greater than the reaction volume of the first half of the cracking tube length, corresponding to the straight sections (2), (3), (4) and (5).

The thermal radiation enclosure of the steam cracking furnace had burners disposed on the walls of the enclosure in five horizontal rows equally spaced out from one another. The total thermal power was distributed between the five rows of burners as follows:

40% of the total thermal power on the first row of burners, disposed at the top of the enclosure adjacent the inlet of the cracking tube, 27% on the second row of burners, disposed immediately below the first row, 18% on the third row of burners, disposed immediately below the second row, 10% on the fourth row of burners, disposed immediately below the third row, and 5% on the fifth row of burners, disposed immediately below the fourth row, adjacent the outlet of the cracking tube. The ratio between the thermal power of the burners applied to the first half of the tube, situated towards the inlet of the enclosure, and that applied to the second half of the tube, situated towards the outlet of such enclosure, was therefore 76/24.

Figure 3:
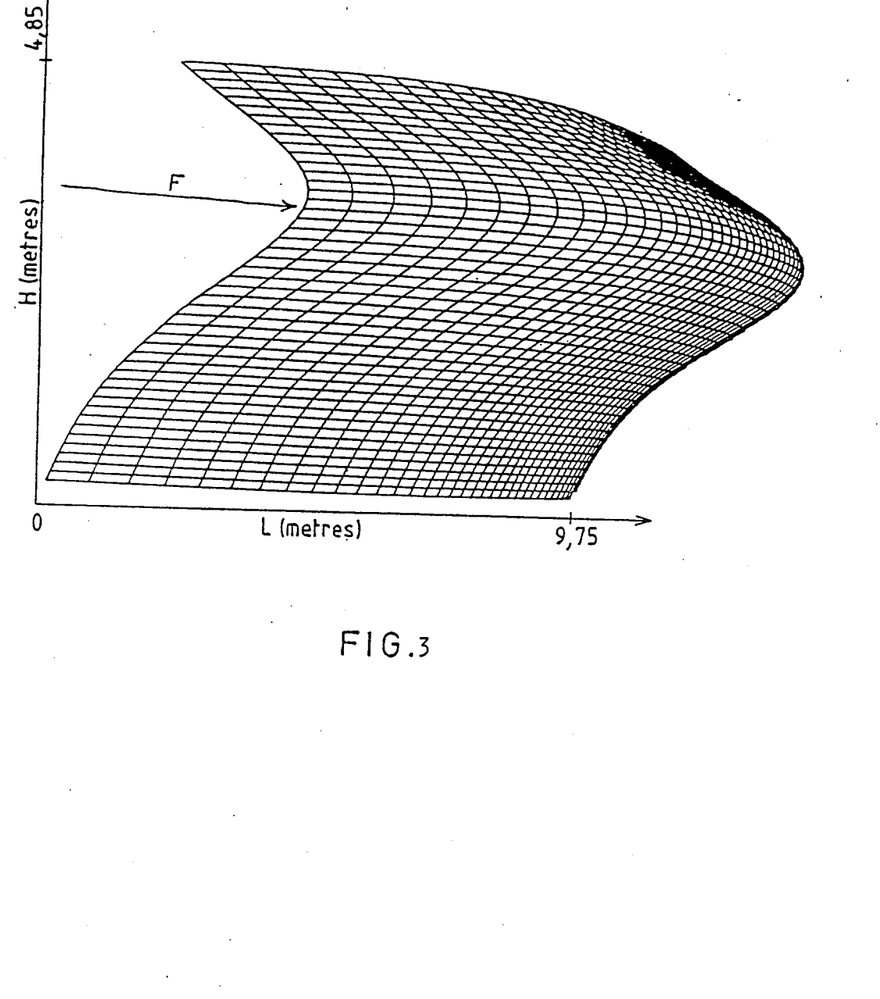
FIGS. 3 and 4 are tridimensional graphs showing the distribution of the thermal flux inside the thermal radiation enclosure of a horizontal steam cracking furnace, such distribution being obtained by a non-homogeneous heating power, such as that disclosed in the present invention, and a homogeneous heating power respectively.

The sheet of heat flux measured inside the thermal radiation enclosure of the furnace was in these conditions represented in FIG. 3 by the surface inscribed in the tridimensional graph connecting via the three coordinate axes the length L of the thermal enclosure, the height H of such enclosure and the heat flux F. FIG. 3 shows more particularly that the maximum of the thermal radiation flux was situated in the upper part of the thermal enclosure, corresponding to the first half of the length of the cracking tube, situated towards the inlet of the thermal radiation enclosure.

A mixture of ethane and steam flowed in the cracking tube. The composition of the mixture of ethane and steam used was such that the ratio by weight between the quantity of ethane and the quantity of steam was 2.25. Ethane was therefore introduced into the cracking tube at a flow rate of 1800 kg/h and steam at a flow rate of 800 kg/h.

The cracking temperature of the mixture of ethane and steam rose from 695° C. at the inlet of the radiation zone of the furnace up to 848° C. at its outlet. The pressure of the mixture was 170 kPa at the furnace outlet. Having regard to the distribution of the thermal flux in the enclosure, the thermal power applied to the first half of the cracking tube length, situated towards the inlet of the radiation zone, was 3.1 times greater than that applied to the second half of the tube length, situated towards the outlet of such zone.

The mean dwell time of the mixture of ethane and steam flowing in the cracking tube between the inlet and outlet of the radiation zone of the furnace was 530 milliseconds.

In these conditions 1200 kg of ethylene were produced per hour and the level of conversion by weight of the steam cracking reaction was 83.5%.

EXAMPLE 2 (FOR COMPARISON)

A steam cracking furnace comprised a thermal radiation enclosure identical in shape and size to that of Example 1. A nickel and chrome base refractory steel cracking tube was disposed in the enclosure and had a total weight substantially identical to the tube of Example 1, an internal diameter of 108 mm, a thickness of 8 mm and, having regard to the capacity of the enclosure and the thermal stresses of the furnace, a total length of 80 metres between the inlet and the outlet of the enclosure. The cracking tube was disposed in the form of a coil comprising 8 horizontal straight portions each of equal length and spaced out via bends. The internal diameter of the straight portions was constant and equal to 108 mm. The internal diameters of the tube of the inlet and the outlet of the enclosure were therefore identical. Similarly, the reaction volume of the first half of the cracking tube length, corresponding to the first four straight portions, was identical with the reaction volume of the second half of the cracking tube length, corresponding to the last four straight portions.

The thermal radiation enclosure of the steam cracking furnace had burners disposed on the enclosure walls in five horizontal rows equally spaced out from one another. The thermal power of the assembly of burners was homogeneously distributed between the five rows. Thus, the ratio between the thermal power of the burners applied to the first half and that applied to the second half of the cracking tube length was 50/50.

Figure 4:
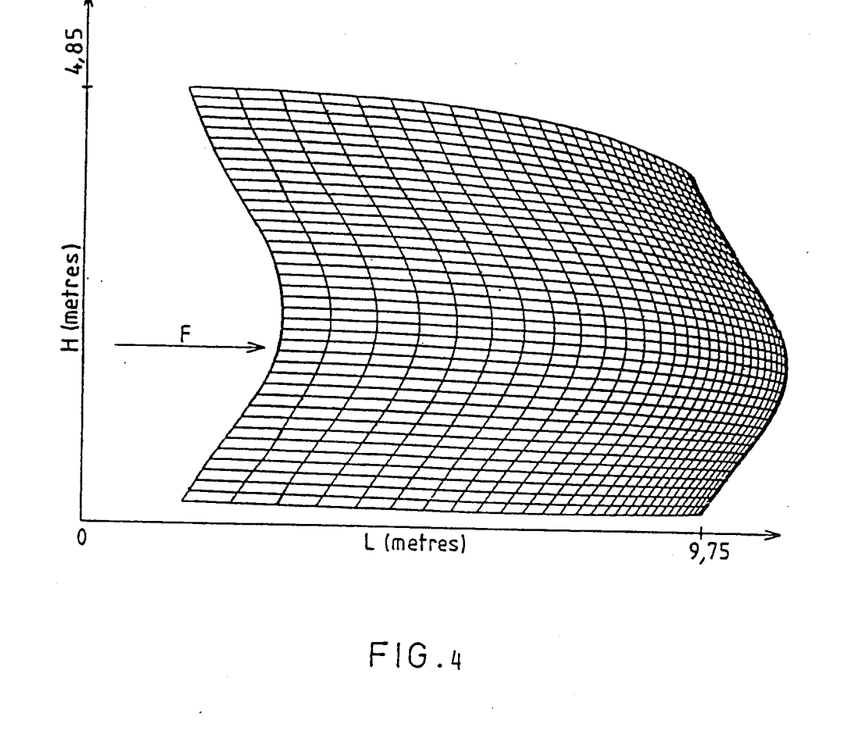

The sheet of heat flux measured inside the thermal radiation enclosure of the furnace is in these conditions represented in FIG. 4 by the surface inscribed in the tridimensional graph connecting via the three coordinate axes the length L of the thermal enclosure, the height H of the enclosure and the heat flux F. FIG. 4 shows more particularly that the maximum of the thermal radiation flux is situated in the relatively central zone of the thermal enclosure.

A mixture of ethane and steam identical with that used in Example 1 flowed in the cracking tube. Ethane was introduced at a flow rate of 1800 kg/h and steam at a flow rate of 800 kg/h.

The cracking temperature of the mixture of ethane and steam was 640° C. at the inlet of the radiation zone of the furnace up to 848° C. at the outlet of such zone. The pressure of the mixture at the outlet of the furnace was 170 kPa. Having regard to the distribution of the heat flux in the enclosure, the thermal power applied to the second half of the cracking tube length was identical with that applied to the first half of the tube length.

The mean dwell time of the mixture of ethane and steam flowing in the cracking tube between the inlet and the outlet of the radiation zone of the furnace was 580 milliseconds.

In these conditions 1085 kg of ethylene was produced per hour, corresponding to a lower production than that obtained in Example 1. The level of conversion by weight of the steam cracking reaction was moreover 75%, a value also lower than that in Example 1.

EXAMPLE 3

Operations were performed in a steam cracking furnace identical with that of Example 1. A mixture formed by gaseous hydrocarbons comprising 64% by weight n-butane, 25% by weight isobutane, 10% by weight 1-butene and 1% by weight isobutene and steam flowed in the cracking tube. The composition of the mixture of gaseous hydrocarbons and steam used was such that the ratio by weight between the quantity of gaseous hydrocarbons and that of steam was 2.3. The gaseous hydrocarbons and the steam were therefore introduced into the cracking tube at flow rates of 2300 kg/h and 1000 kg/h respectively.

The cracking temperature of the mixture rose from 620° C. at the entry of the radiation zone of the furnace to 836° C. at the outlet of the furnace. The pressure of the mixture at the outlet of the furnace was 185 kPa.

The thermal power applied to the first half of the length of the cracking tube was 3.1 times greater, as in Example 1, than that applied to the second half of the tube length. The mean dwell time of the mixture flowing in the cracking tube was 580 milliseconds between the inlet and outlet of the radiation zone of the furnace.

In these conditions 700 kg of ethylene was produced per hour and the level of conversion by weight of the steam cracking reaction was 98%.

EXAMPLE 4 (FOR COMPARISON)

Operations were performed in a steam cracking furnace identical to that of Example 2. A mixture identical with that used in Example 3 flowed in the cracking tube at flow rates also identical to those of Example 3.

The cracking temperature of the mixture rose from 580° C. at the inlet of the radiation zone of the furnace to 836° C. at its outlet. The pressure of the mixture at the outlet of the furnace was 185 kPa. The thermal power applied to the first half of the cracking tube length was identical, as in Example 2, to that applied to the second half of the tube length.

The mean dwell time of the mixture flowing in the cracking tube was 635 milliseconds between the inlet and outlet of the radiation zone of the furnace.

In these conditions 610 kg of ethylene was produced per hour, corresponding to a production lower than that obtained in Example 3. The level of conversion by weight of the steam cracking reaction was also 93%, another lower value than in Example 3.

EXAMPLE 5

A vertical steam cracking furnace comprised a brickwork thermal radiation enclosure formed by a rectangular parallelipiped whose internal dimensions were length: 9.75 mm; width: 1.60 mm and height: 9.60 m. A nickel and chromium based stainless steel cracking tube was disposed in the enclosure and had a mean internal diameter of 98.5 mm, a thickness of 8 mm and, having regard to the capacity of the enclosure, a total length of 64 m. The ratio between the length and the mean internal diameter was 650. The cracking tube was disposed in the form of a coil comprising 8 vertical straight portions each of equal length and interconnected via bends. The internal diameter of the first two portions disposed towards the inlet of the thermal enclosure was 76 mm; the two following sections had an internal diameter of 84 mm; the following two sections had an internal diameter of 104 mm; and finally the internal diameter of the last two sections disposed towards the outlet of the thermal enclosure was 130 mm.

The internal diameters of the cracking tube at the inlet and outlet of the thermal radiation enclosure being 76 mm and 130 mm respectively, the ratio between the internal diameters of the tube at the inlet and outlet was therefore 1.7. Moreover, the reaction volume of the second half of the length of the cracking tube, corresponding to the first four straight portions, was 2.16 times greater than the reaction volume of the first half of the cracking tube length, corresponding to the last four straight portions.

The thermal radiation enclosure of the steam cracking furnace had burners disposed on the enclosure walls in five vertical rows equally spaced out from one another. The thermal power of the burners was so distributed along the cracking tube that the first half of the tube length, corresponding to the first four straight portions, received 70% of the total thermal power, while the second half of the tube length, corresponding to the last four straight portions, received 30% of the total thermal power.

A mixture of liquid hydrocarbons and steam flowed in the cracking tube. The liquid hydrocarbons were formed by a naphtha of density 0.684, having an ASTM distillation range of 45°/185° C. and contents by weight of 38.2% linear paraffin waxes, 36.9% branched paraffin waxes, 17.1% cyclane compounds and 7.8% aromatic compounds. The composition of the mixture of naphtha and steam used was such that the ratio by weight between the quantity of naphtha and the quantity of steam was 2.1. The naphtha was therefore introduced into the cracking tube at a flow rate of 2100 kg/h and the steam at a flow rate of 1000 kg/h.

Figure 2:
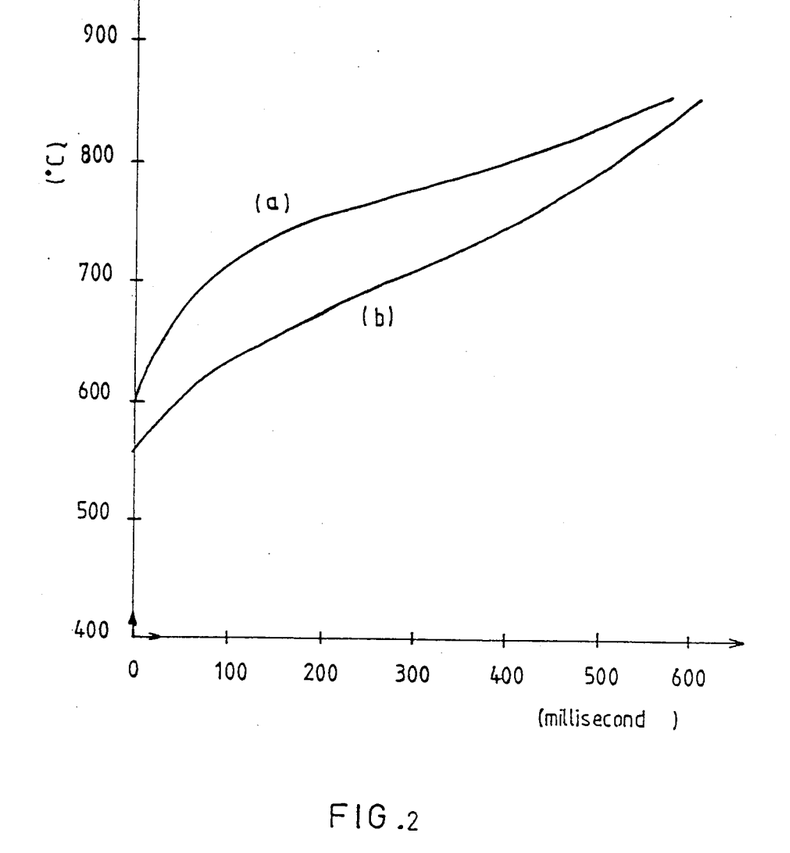
FIG. 2 is a graph showing the increase in the cracking temperature of the mixture of hydrocarbons and steam flowing in a cracking tube from the inlet to the outlet of the radiation zone of a steam cracking furnace as a function of the mean dwell time of the mixture flowing in the tube.

The cracking temperature of the mixture of naphtha and steam rose from 600° C. at the inlet of the radiation zone of the furnace up to 846° C. at its outlet. The development of the cracking temperature of the mixture along the cracking tube is described by curve (a) in FIG. 2, showing on the abscissa axis the mean dwell time (in milliseconds) of the mixture flowing in the cracking tube from the inlet to the outlet of the radiation zone of the furnace, and on the ordinate axis the cracking temperature (in ° C.) of the mixture. The curve (a) shows that the cracking temperature of the mixture increases in its initial portion relatively quickly as a function of the mean dwell time. The maximum skin temperature along the cracking tube was 1000° C. The pressure of the mixture at the furnace outlet was 170 kPa. Having regard to the distribution of the heat flux in the thermal radiation enclosure, the thermal power applied to the first half of the length of the cracking tube, situated towards the inlet of the radiation zone, was 2.3 time greater than that applied to the second half of the tube length, situated towards the outlet of such zone.

The mean dwell time of the mixture of naphtha and steam flowing in the cracking tube between the inlet and the outlet of the furnace radiation zone was 560 milliseconds.

In these conditions 567 kg of ethylene were produced per hour and the cracking yield of ethylene was 27%. The level of conversion by weight of naphtha was 73%.

EXAMPLE 6 (FOR COMPARISON)

A vertical steam cracking furnace comprised a thermal radiation enclosure identical in shape and size to that of Example 5. A nickel and chromium based refractory steel cracking tube was disposed in the enclosure and had an internal diameter of 98.5 mm, a thickness of 8 mm and a total length of 64 metres between the inlet and outlet of the enclosure. The ratio between the length and the internal diameter of the tube was 650. The cracking tube was disposed in the form of a coil comprising 8 vertical straight portions each of equal length and interconnected via bends. The internal diameter of the straight sections was constant and equal to 98.5 mm. The internal diameters of the tube at the inlet and outlet of the enclosure were therefore identical. Similarly, the reaction volume of the first half of the cracking tube length, corresponding to the first four straight portions, was identical with the reaction volume of the second half of the cracking tube length, corresponding to the last four straight portions.

The thermal radiation enclosure of the steam cracking furnace had burners disposed on the enclosure walls. The thermal power of the assembly of burners was homogeneously distributed along the cracking tube, so that the ratio between the thermal power of the burners applied to the first half and that applied to the second half of the cracking tube length was 50/50.

A mixture of naphtha and steam identical with that used in Example 5 flowed in the cracking tube. The naphtha was introduced at a flow rate of 2100 kg/h and the steam at a flow rate of 1000 kg/h.

The cracking temperature of the mixture of naphtha and steam rose from 560° C. at the inlet of the radiation zone of the furnace up to 846° C. at its outlet. The development of the cracking temperature of the mixture along the tube is described by curve (b) in FIG. 2. Curve (b) shows that the cracking temperature of the mixture increases in its initial portion relatively slowly as a function of the mean dwell time. The maximum skin temperature along the cracking tube was 1020° C. The pressure of the mixture at the outlet of the furnace was 170 kPa.

The mean dwell time of the mixture of naphtha and steam flowing in the cracking tube between the inlet and the outlet of the radiation zone of the furnace was 610 milliseconds.

In these conditions 504 kg of ethylene were produced per hour and the cracking yield of ethylene was 24%. The level of conversion by weight of naphtha was 70.4%.

We claim:

1. A process for the preparation of olefins and diolefins by the cracking of hydrocarbons in the presence of steam, wherein a mixture of hydrocarbons and steam flowing in a cracking tube disposed inside a furnace radiation zone is passed through such zone in a dwell time of between 300 and 1800 milliseconds at a furnace outlet pressure of between 120 and 240 kPa, the process being characterized in that
   (a) the cracking temperature of the mixture of hydrocarbons and steam increases from the inlet temperature of the radiation zone of between 500° and 700° C. to the outlet temperature of such zone of between 800° and 880° C., the increase in temperature being associated with a non-homogeneous distribution of the thermal power of the furnace applied along the cracking tube, the distribution being such that the thermal power applied to the first half of the tube length, situated towards the inlet of the radiation zone, is 1.5 to 5 times greater than that applied to the second half of the tube length, situated towards the outlet of such zone, and
   (b) the reaction volume of the second half of the length of the cracking tube, situated towards the outlet of the radiation zone, is 1.3 to 4 times greater than that of the first half of the tube length, situated towards the inlet of such zone.

2. A process according to claim 1, characterized in that the thermal power applied to the first half of the tube length is 1.5 to 4 times greater than that applied to the second half of the tube length.

3. A process according to claim 1, characterized in that the reaction volume of the second half of the length of the cracking tube is 1.5 to 2.5 times greater than that of the first half of the tube length.

4. A process according to claim 1, characterized in that the hydrocarbons used comprise liquid hydrocarbons selected from naphtha, light gasolines, gas oil, and their mixtures with saturated and unsaturated hydrocarbons having 3 to 6 carbon atoms.

5. A process according to claim 1, charaterized in that the composition of the mixture of hydrocarbons and steam used is such that the ratio by weight between the quantity of hydrcarbons and the quantity of steam is between 1 to 10.

6. A process according to claim 1 characterized in that the hydrocarbons used comprise gaseous hydrocarbons formed by alkanes having 2 to 4 carbon atoms or by their mixtures.

7. A process according to claim 6 wherein said alknes having 2 to 4 carbon atoms are mixed with alkanes or alkenes selected from the group consisting of alkenes having 2 to 6 carbon atoms, methane, alkanes having 5 to 6 carbon atoms, and mixtures thereof.

8. A process according to claim 1 characterized in that the hydrocarbons used are selected from the group consisting of natural gas, liquified petroleum gas, ethane, byproduct of steam cracking of naphtha or gas oil, and mixtures thereof.

* * * * *

UNITED STATES PATENT AND TRADEMARK OFFICE
CERTIFICATE OF CORRECTION

PATENT NO. : 4,762,958

DATED : August 9, 1988

INVENTOR(S) : Andre Martens, Serge Bellet

It is certified that error appears in the above-identified patent and that said Letters Patent is hereby corrected as shown below:

Col. 6, l. 67, "diameter of 88 mm;" should read --diameter of 99 mm;--

Signed and Sealed this

Fourteenth Day of March, 1989

Attest:

DONALD J. QUIGG

*Attesting Officer*  *Commissioner of Patents and Trademarks*